United States Patent
Sookraj

(12) 
(10) Patent No.: US 6,228,798 B1
(45) Date of Patent: May 8, 2001

(54) PROCESS FOR PRODUCING A VANADIUM PHOSPHORUS OXIDE CATALYST

(75) Inventor: Sadesh H Sookraj, Vanderbijlpark (ZA)

(73) Assignee: Sasol Technology (Proprietary) Limited, Johannesburg (ZA)

( * ) Notice: Subject to any disclaimer, the term of this patent is extended or adjusted under 35 U.S.C. 154(b) by 0 days.

(21) Appl. No.: 09/308,573

(22) PCT Filed: Jun. 3, 1998

(86) PCT No.: PCT/GB98/01616

§ 371 Date: May 21, 1999

§ 102(e) Date: May 21, 1999

(87) PCT Pub. No.: WO98/55226

PCT Pub. Date: Dec. 10, 1998

(30) Foreign Application Priority Data

Jun. 4, 1997 (ZA) .................................................. 97/4925
Jan. 26, 1998 (ZA) .................................................. 98/0614

(51) Int. Cl.$^7$ ........................... B01J 31/00; B01J 27/198; B01J 27/192; B01J 23/00; B01J 23/16

(52) U.S. Cl. ..................... 502/209; 502/162; 502/210; 502/212; 502/213; 502/312; 502/313; 502/314; 502/353

(58) Field of Search .................. 502/209–213, 502/305, 306, 311, 312, 313, 314, 353, 162

(56) References Cited

U.S. PATENT DOCUMENTS

| | | | | |
|---|---|---|---|---|
| 5,225,389 | * | 7/1993 | Caillod et al. | 502/205 |
| 5,288,880 | | 2/1994 | Matsuura | 549/260 |
| 5,300,707 | * | 4/1994 | Caillod et al. | 568/480 |
| 5,750,777 | * | 5/1998 | Aubry et al. | 562/549 |

FOREIGN PATENT DOCUMENTS

| | | |
|---|---|---|
| 0608837 | 8/1994 | (EP) . |
| 0794151 | 9/1997 | (EP) . |
| 0799795 | 10/1997 | (EP) . |

* cited by examiner

Primary Examiner—Mark L. Bell
Assistant Examiner—Patricia L. Hailey
(74) Attorney, Agent, or Firm—Ladas & Parry

(57) ABSTRACT

A method of making a vanadium phosphorus oxide (VPO) catalyst by precipitating from a 45–65 g/l solution of $V^{4+}$ ions and $V^{5+}$ ions a vanadium- and phosphorus-containing precipitate comprising a complex of formula $VOHPO_4$. The precipitate is calcined under an inert atmosphere to produce a VPO catalyst whole active phase is formula $(VO)_2P_2O_9$. Said solution comprises cations of at least two of Bi, Zr, Cr, Ce, Co, Mn, Mg and Mo such that the precipitate comprises 1–25% by mass of said dopant metal cations in total, the balance being said complex. Each dopant metal forms 0.1–20% by mass of the precipitate.

17 Claims, No Drawings

PROCESS FOR PRODUCING A VANADIUM PHOSPHORUS OXIDE CATALYST

This invention relates to vanadium phosphorus oxide (VPO) catalysts. More particularly, the invention relates to a method of making VPO catalyst suitable for the oxidation of $C_4$ and $C_5$ paraffins and olefins to maleic anhydride, phthalic anhydride and acetic acid, especially paraffins and olefins produced by Fischer-Tropsch processes, and to a VPO catalyst made in accordance with the method.

According to the invention there is provided a method of making a vanadium phosphorus oxide (VPO) catalyst, the method comprising the steps of:

precipitating, from a solution comprising dissolved $V^{4+}$ ions and $V^{5+}$ ions at a total concentration of 45–65 g/l, a vanadium-containing and phosphorus-containing precipitate comprising a complex in accordance with the formula $VOHPO_4 \cdot \frac{1}{2}H_2O$; and calcining the precipitate under an inert atmosphere, to produce a VPO catalyst having an active phase in accordance with the formula $(VO)_2P_2O_9$, the solution from which the precipitate is precipitated comprising dissolved cations of at least two dopant metals selected from the group consisting of Bi, Zr, Cr, Ce, Co, Mn, Mg and Mo, said dissolved dopant metal cations being present in the solution in proportions such that the precipitate comprises 1–25% by mass of dopant metal cations in total, the balance being the $VOHPO_4 \cdot \frac{1}{2}H_2O$ complex, each dopant metal forming 0.1–20% by mass of the precipitate.

Preferably, the proportion of dissolved $V^{4+}$ ions relative to the proportion of dissolved $V^{5+}$ ions is as high as practically feasible. Furthermore, the ratio of dissolved $V^{4+}$ ions:$V^{5+}$ ions in the solution may be such that the molar proportion of each of the $V^{4+}$ ions and the $V^{5+}$ ions in VPO catalyst, after calcining, is 0.1–10 mole %, typically 0.5–5%.

Preferably the total concentration of dissolved $V^{4+}$ ions and $V^{5+}$ ions in the solution is 50–60 g/l, the dissolved dopant metal cations being present in the solution in proportions such that the precipitate comprises 2–20% by mass of the dopant metals in total, each dopant metal forming 0.5–15% by mass of the precipitate, the ratio of dissolved $V^{4+}$ ions:$V^{5+}$ ions in the solution being such that the molar proportion of $V^{5+}$ ions in the VPO catalyst is 0.1–10 mole %, typically 0.5–6 mole %.

The solution from which the precipitate is precipitated may comprise dissolved cations of 2–3 dopant metals selected from said group consisting of Bi, Zr, Cr, Ce, Co, Mn, Mg and Mo.

One of the dopant metals may be Bi, Bi cations being present in the solution from which the precipitate is precipitated in a proportion such that Bi forms 1–15% by mass of the precipitate, the solution comprising, in addition to the Bi cations, cations of 1–2 other dopant metals selected from:
Zr;
Mn and Ce;
Co;
Ce;
Zr and Ce; and
Zr and Co.

Instead, one of the dopant metals may be Zr, Zr cations being present in the solution from which the precipitate is precipitated in a proportion such that Zr forms 1–15% by mass of the precipitate, the solution comprising, in addition to the Zr cations, cations of 1–2 other dopant metals selected from:
Bi;
Cr;
Ce and Cr;
Ce;
Co;
Bi and Ce; and
Bi and Co.

Instead, one of the dopant metals may be Cr, Cr cations being present in the solution from which the precipitate is precipitated in a proportion such that Cr forms 1–15% by mass of the precipitate, the solution comprising, in addition to the Cr cations, cations of 1–2 other dopant metals, selected from:
Zr; and
Ce and Zr.

Instead, one of the dopant metals may be Ce, Ce cations being present in the solution from which the precipitate is precipitated in a proportion such that Ce forms 1–15% by mass of the precipitate, the solution comprising, in addition to the Ce cations, cations of 1–2 other dopant metals, selected from:
Zr and Cr;
Zr;
Bi and Mn;
Bi;
Bi and Zr; and
Mn and Mg.

Instead, one of the dopant metals may be Co, Co cations being present in the solution from which the precipitate is precipitated in a proportion such that Co forms 1–15% by mass of the precipitate, the solution comprising, in addition to the Co cations, cations of 1–2 other dopant metals, selected from:
Zr;
Bi; and
Bi and Zr.

Instead, one of the dopant metals may be Mn, Mn cations being present in the solution from which the precipitate is precipitated in a proportion such that Mn forms 1–15% by mass of the precipitate, the solution comprising, in addition to the Mn cations, cations of 1–2 other dopant metals, selected from:
Bi and Ce;
Mg and Ce; and
Mo.

Instead, one of the dopant metals may be Mg, Mg cations being present in the solution from which the precipitate is precipitated in a proportion such that Mg forms 1–20% by mass of the precipitate, the solution comprising cations of Mn and Ce dopant metals in addition to the Mg cations.

Instead, one of the dopant metals may be Mo, Mo cations being present in the solution from which the precipitate is precipitated in a proportion such that Mo forms 1–20% by mass of the precipitate, the solution comprising cations of Mn dopant metal in addition to the Mo cations.

The solution may comprise a solvent selected from alcohols and mixtures of two or more alcohols. When the solvent is a mixture of two alcohols, the alcohols may be present in a mass ratio of 1:2–2:1. In particular, the solvent may be anhydrous, the alcohol being selected from:
isobutanol;
benzyl alcohol;
ethanol;
octanol;
2-butanol;
isopropanol; and
mixtures of any two or more thereof.

More particularly, the solvent may be a mixture of two said alcohols.

The method may include the preliminary step of obtaining the solution of the $V^{4+}$ ions and $V^{5+}$ ions in the solution by dissolving $V^{5+}$ ions in the solvent and reducing a portion of the $V^{5+}$ ions to $V^{4+}$ ions. Reducing the $V^{5+}$ cations to the $V^{4+}$ cations may be by using a suitable reducing agent.

Dissolving the $V^{5+}$ ions in the solvent may be by admixing vanadium pentoxide ($V_2O_5$) with the solvent. When the solvent is an alcohol and is anhydrous, the reducing agent may be selected from benzyl alcohol, isobutanol or isopropranol, eg so that the solvent and reducing agent are the same alcohol. The reducing may be by refluxing the solution (conveniently at atmospheric pressure), optionally followed by stirring, at a suitable temperature, followed by the precipitation. In particular, the reducing of the $V^{5+}$ ions to $V^{4+}$ ions may be by means of a reducing agent, the method including refluxing the solvent containing the $V^{5+}$ ions dissolved therein with the reducing agent, the solvent and reducing agent optionally being the same alcohol.

The precipitation may be effected by adding phosphate ions to the solution, eg by adding phosphoric acid to the solution.

For the purpose of the reducing, routine experimentation can be employed to determine a suitable reducing agent and to determine a suitable proportion thereof to be used, to determine suitable periods respectively for refluxing and stirring, to determine a suitable stirring temperature, and to determine a suitable refluxing pressure and temperature if refluxing is at a pressure other than atmospheric pressure. After the refluxing has been carried out for a desired period, eg 3–20 hours, preferably 6–15 hours, and the stirring has been carried out for a desired period, eg 12–36 hours, preferably 18–30 hours, to take the reduction to a desired degree of completion, the solution may be cooled to room or ambient temperature, the precipitated complex then being collected and washed and dried, prior to calcining thereof.

Preferably, the calcining is carried out under an inert atmosphere for example under argon, eg in an oven flushed by argon, according to a suitable heating regime. Thus, heating rates, cooling rates, maximum temperature and the temperatures and durations of any temperature holds or plateaus may be determined by routine experimentation, a maximum temperature of 400–500° C., preferably 420–480° C., eg 450° C. being suitable. Thus the calcining may include heating the precipitate under an inert atmosphere to a maximum temperature of 400–500° C.

The dopant metal cations may be dissolved in the solvent by dissolving a suitable dopant compound (also known as a promoter compound, the dopant cations also being known as promoter cations) in the solvent. Suitable dopant compounds are as follows:
For Bi cations, $(BiO)_2.Co_3$, can be used;
For Zr cations, $ZrOCl_2.8H_2O$, $ZrOCl_2$, can be used;
For Cr cations, $CrO_3$, can be used;
For Ce cations, $Ce(NO_3)_3.6H_2O$, can be used;
For Co cations, $Co_3(PO_4)_2.8H_2O$, can be used;
For Mn cations, $MnCl_2.4H_2O$, can be used;
For Mg cations, $MgO$, can be used; and
For Mo cations, $MoO_3$, can be used.

The invention extends to a VPO catalyst, whenever made in accordance with the method described above.

The invention will now be described, by way of non-limiting illustrative example, with reference to the following Examples. In the Examples, unless otherwise specified, refluxing, stirring and calcining were carried out at atmospheric pressure; and room (ambient) temperature was 20–25° C.

EXAMPLE 1

$VOHPO_4.½H_2O$ (97.5% by mass)+1% Bi promoter+ 1.5% Zr promotors:

A solvent comprising 90 ml benzyl alcohol and 60 ml isobutanol was used to dissolve 15 g of $V_2O_5$, 0.14 g of $ZrOCl_2.8H_2O$ and 0.211 g of $(BiO)_2.CO_3$. The solution so formed was refluxed for 7 hours at atmospheric pressure after which it was stirred for 16 hours at room temperature. 26 g of 98% by mass $H_3PO_4$ was added to the solution and the mixture was stirred under reflux for 3 hours. The solution was cooled to room temperature and a precipitate which had formed in response to the $H_3PO_4$ addition was recovered by filtration. The precipitate was washed thoroughly with water (about 5 l). A blue solid was obtained which as oven-dried for 12 hours at 150° C. to form a catalyst precursor.

The catalyst precursor was calcined in an inert atmosphere in a reaction vessel in the form of an oven. Argon was used as the inert atmosphere, a flow rate of argon of approximately 6 ml/min being used to flush the vessel. The temperature was steadily increased from room temperature to 300° C. over a 3-hour period, ie at a rate of roughly 100° C./hour. The temperature was maintained at 300° C. for 2 hours. The temperature was then steadily increased to 450° C. over a further 3 hours at a rate of about 50° C./hour. The temperature was maintained at 450° C. for 6 hours. The temperature was then steadily reduced to room temperature over a period of 3 hours at a rate of about 150° C./hour, to form a novel VPO catalyst.

A micro-reactor was loaded with the novel VPO catalyst so formed. Butane, at a concentration of 1.3% by volume in air, was fed over the catalyst in the micro-reactor at a gas hourly space velocity of 1500–3000 $h^{-1}$, preferably 2000–2700 $h^{-1}$. The temperature for maximum maleic anhydride yield was found to be between 300 and 450° C., preferably between 390° C. and 410° C. It was surprising to note that, when the catalyst was used to catalyze butane conversion to maleic anhydride, after one day the butane conversion was 67% and the selectivity to produce maleic anhydride was 36%. It was found that the VPO catalyst out-performed a control (standard) VPO catalyst by a considerable margin as set forth in Table 1 hereunder.

TABLE 1

Comparison of Standard and Novel VPO Catalysts at Equilibration

|  | Standard VPO | Novel VPO |
| --- | --- | --- |
| % butane conversion | 31% | 80% |
| % selectivity to produce maleic anhydride | 54% | 70% |
| % selectivity to produce carbon oxides | 46% | 30% |
| % yield | 16.7% |  |

These novel catalysts were tested regarding their ability to catalyze the conversion of butene to maleic anhydride, pentane to maleic anhydride and phthalic anhydride, and pentene to maleic anhydride and phthalic anhydride as set forth in Table 2 hereunder.

TABLE 2

Comparison of Novel VPO Catalysts at Equilibration

| | Butane | Pentane | Pentene |
|---|---|---|---|
| Gas hourly space velocity (h$^{-1}$) | 1500–3000, preferably 2000–2600 | 750–2000, preferably 800–1500 | 750–2000, preferably 1500–1800 |
| Temperature for maximum yield (° C.) | 350–450 preferably 380–410 | 320–380 preferably 330–350 | 300–380 preferably 310–340 |
| % Conversion | 80 | 82 | 90 |
| % Maleic anhydride selectivity | 65 | 30 | 32 |
| % Phthalic anhydride selectivity | — | 8 | 10 |

EXAMPLE 2

$VOHPO_4.\frac{1}{2}H_2O$ (97% by mass)+1.5% Zr promoter+ 1.5% Cr promoter:

A solvent comprising 90 ml benzyl alcohol and 60 ml isobutanol was used to dissolve 15 g of $V_2O_5$, 0.124 g of $CrO_3$ and 0.4 g of $ZrOCl_2.8H_2O$. The solution so formed was refluxed for 7 hours and was then stirred for 16 hours at room temperature, 24 g of 98% $H_3PO_4$ was added to the solution, followed by stirring under reflux for 3 hours. The solution was then cooled to room temperature and a precipitate which had formed was recovered by filtration. The precipitate was washed thoroughly with water (about 5 l). A blue solid was obtained which was over-dried for 12 hours at 150° C. to form a catalyst precursor.

EXAMPLE 3

$VOHPO_4.\frac{1}{2}H_2O$ (88.5% by mass)+8.5% Ce promoter+ 1.5% Zr promoter+1.5% Cr promoter:

A solvent comprising 90 ml benzyl alcohol and 60 ml isobutanol was used to dissolve 15 g of $V_2O_5$, 0.4 g of $ZrOCl_2$, 0.124 g of $CrO_3$ and 3.04 g of $Ce(NO_3)_3.6H_2O$. The solution so formed was refluxed for 7 hours and was then stirred for 16 hours at room temperature. 24 g of 98% $H_3PO_4$ was added to the solution followed by stirring under reflux for 3 hours. The solution was cooled to room temperature and a precipitate which had formed was recovered by filtration. The precipitate was washed thoroughly with water (about 5 l). A blue solid was obtained which was oven-dried for 12 hours at 150° C. to form a catalyst precursor.

EXAMPLE 4

$VOHPO_4.\frac{1}{2}H_2O$ 90% by mass)+1.5% Zr promoter+8.5% Ce promoter:

A solvent comprising 90 ml benzyl alcohol and 60 ml isobutanol was used to dissolve 15 g of $V_2O_5$, 0.4 g of $ZrOCl_2.8H_2O$ and 3.04 g of $Ce(NO_3)_3.6H_2O$. The solution so formed was refluxed for 7 hours and then stirred for 16 hours at room temperature. 26 g and 98% $H_3PO_4$ was added to the solution followed by stirring under reflux for 3 hours. The solution was then cooled to room temperature and a precipitate which had formed was recovered by filtration. The precipitate was washed thoroughly with water (about 5 l). A blue solid was obtained which was oven-dried for 12 hours at 150° C. to form a catalyst precursor.

EXAMPLE 5

$VOHPO_4.\frac{1}{2}H_2O$ (92% by mass)+1.5% Zr promoter+ 1.5% Cr promoter+5% Ce promoter:

A solvent comprising 90 ml benzyl alcohol and 60 ml isobutanol was added to 15 g to $V_2O_5$, 1.79 g of $Ce(NO_3)_3.6H_2O$, 0.4 g of $ZrOCl_2.8H_2O$ and 0.124 g of $CrO_3$. The solution so formed was refluxed for 7 hours and was then stirred for 16 hours at room temperature. 23 g of 98% $H_3PO_4$ was added to the solution. The solution was cooled to room temperature and a precipitate which had formed was recovered by filtration. The precipitate was washed thoroughly with water (about 5 l). A blue solid was obtained which was oven-dried for 12 hours at 150° C. to form a catalyst precursor.

EXAMPLE 6

$VOHPO_4.\frac{1}{2}H_2O$ (90% by mass)+1.5% Zr promoter+ 8.5% Co promoter:

A solvent comprising 90 ml benzyl alcohol and 60 ml isobutanol was used to dissolve 15 g of $V_2O_5$ and 0.4 g of $ZrOCl_2.8H_2O$. The solution so formed was refluxed for 7 hours and was then stirred for 16 hours at room temperature. 26 g of 98% $H_3PO_4$ was added to the solution followed by the addition of 1.2 g of $Co_3(PO_4)_2.8H_2O$ after which the solution was stirred under reflux for 3 hours. The solution was then cooled to room temperature and a precipitate which had formed was recovered by filtration. The precipitate was washed thoroughly with water (about 5 l). A blue solid was obtained which was over-dried for 12 hours at 150° C. to form a catalyst precursor.

EXAMPLE 7

$VOHPO_4.\frac{1}{2}H_2O$ (89% by mass)+1% Bi promoter+5% Mn promoter+5% Ce promoter:

A solvent comprising 90 ml benzyl alcohol and 60 ml isobutanol was used to dissolve 15 g of $V_2O_5$, 0.82 g of $MnCl_2.4H_2O$, 1.79 g of $Ce(NO_3)_3.6H_2O$ and 0.211 g of $(BiO)_2.CO_3$. The solution so formed was refluxed for 7 hours and was then stirred for 16 hours at room temperature. 24 g of 98% $H_3PO_4$ was then added to the solution followed by stirring under reflux for 3 hours. The solution was then cooled to room temperature and a precipitate which had formed was recovered by filtration. The precipitate was washed thoroughly with water (about 5 l). A blue solid was obtained which was oven-dried for 12 hours at 150° C. to form a catalyst precursor.

EXAMPLE 8

$VOHPO_4.\frac{1}{2}H_2O$ (90.5% by mass)+1% Bi promoter+ 8.5% Co promoter:

A solvent comprising 90 ml benzyl alcohol and 60 ml isobutanol was used to dissolve 15 g of $V_2O_5$ and 0.211 g of $(BiO)_2.CO_3$. The solution so formed was refluxed for 7 hours and then stirred for 16 hours at room temperature, 26 g of 98% $H_3PO_4$ was added to the solution followed by the addition of 1.2 g of $Co_3(PO_4)_2.8H_2O$, followed by turn by stirring under reflux for 3 hours. The solution was then cooled to room temperature and a precipitate which had formed was recovered by filtration. The precipitate was washed thoroughly with water (about 5 l). A blue solid was obtained which was oven-dried for 12 hours at 150° C. to form a catalyst precursor.

EXAMPLE 9

VOHPO$_4$.½H$_2$O (90.5% by mass)+1% Bi promoter+8.5% Ce promoter:

A solvent comprising 90 ml benzyl alcohol and 60 ml isobutanol was used to dissolve 15 g of V$_2$O$_5$, 3.04 g of Ce(NO$_3$)$_3$.6H$_2$O and 0.211 g of (BiO)$_2$.CO$_3$. The solvent so formed was refluxed for 7 hours after which it was stirred for 16 hours at room temperature. 26 g of 98% H$_3$PO$_4$ was added to the solution followed by stirring under reflux for 3 hours. The solution was cooled to room temperature and a precipitate which had formed was recovered by filtration. The precipitate was washed thoroughly with water (about 5 l). A blue solid was obtained which was oven-dried for 12 hours at 150° C. to form a catalyst precursor.

EXAMPLE 10

VOHPO$_4$.½H$_2$O (89% by mass)+1% Bi promoter+1.5% Zr promoter+8.5% Ce promoter:

A solvent comprising 90 ml benzyl alcohol and 60 ml isobutanol was used to dissolve 15 g of V$_2$O$_5$, 0.4 g of ZrOCl$_2$.8H$_2$O, 3.04 g of Ce(NO$_3$)$_3$.6H$_2$O and 0.211 g of (BiO)$_2$.CO$_3$. The solution to formed was refluxed for 7 hours and then stirred for 16 hours at room temperature. 28 g of 98% H$_3$PO$_4$ was added to the solution followed by stirring under reflux for 3 hours. The solution was cooled to room temperature and a precipitate which had formed was recovered by filtration. The precipitate was washed thoroughly with water (about 5 l). A blue solid was obtained which was oven-dried for 12 hours at 150° C. to form a catalyst precursor.

EXAMPLE 11

VOHPO$_4$.½H$_2$O (89%)+1% Bi promoter+1.5%Zr promoter+8.5% Co promoter:

A solvent comprising 90 ml benzyl alcohol and 60 ml isobutanol was used to dissolve 15 g of V$_2$O$_5$, 0.4 g of ZrOCl$_2$.8H$_2$O and 0.211 g of (BiO)$_2$.CO$_3$. The solution so formed was refluxed for 7 hours and then stirred for 16 hours at room temperature. 27 g of 98% H$_3$PO$_4$ was added to the solution followed by the addition of 1.2 g of Co$_3$(PO$_4$)$_2$.8H$_2$O followed in turn by stirring under reflux for 3 hours. The solution was cooled to room temperature and a precipitate which had formed was recovered by filtration. The precipitate was washed thoroughly with water (about 5 l). A blue solid was obtained which was oven-dried for 12 hours at 150° C. to form a catalyst precursor.

EXAMPLE 12

VOHPO$_4$.½H$_2$O (85% by mass)+5% Mn promoter+5% Mg promoter+5% Ce promoter:

A solvent comprising 90 ml benzyl alcohol and 60 ml isobutanol was used to dissolve 15 g of V$_2$O$_5$, 0.167 g of MgO, 1.79 g of Ce(No$_3$)$_3$.6H$_2$O and 0.82 g of MnCl$_2$.4H$_2$O. The solution so formed was refluxed for 7 hours after which it was stirred for 16 hours at room temperature. 27 g of 98% H$_3$PO$_4$was added followed by the addition of 1.2 g of Co$_3$(PO$_4$)$_2$.8H$_2$O, followed in turn by stirring under reflux for 3 hours. The solution was cooled to room temperature and a precipitate was obtained which was recovered by filtration. The precipitate was washed thoroughly with water (about 5 l). A blue solid was oven dried for 12 hours at 150° C. to form a catalyst precursor.

EXAMPLE 13

VOHPO$_4$.½H$_2$O (90% by mass)+5% Mo promoter+5% Mn promoter:

A solvent comprising of 90 ml benzyl alcohol and 60 ml isobutanol was used to dissolve 15 g of V$_2$O$_5$, 0.82 g of MnCl$_2$.4H$_2$O and 0.6 g of MoO$_3$. The solution so formed was refluxed for 7 hours and then stirred for 16 hours at room temperature. 27 g of 98% H$_3$PO$_4$ was added, followed by the addition of 1.2 g of Co$_3$(PO$_4$)$_2$.8H$_2$O, followed in turn by stirring under reflux for 3 hours. The solution was cooled to room temperature and a precipitate was obtained which was removed by filtration. The precipitate was washed thoroughly with water (about 5 l). A blue solid was oven-dried for 12 hours at 150° C. to obtain a catalyst precursor.

With regard to Examples 1–13 it should be noted that the benzyl alcohol and isobutanol were fully miscible and formed a solvent to which the V$_2$O$_5$ was added to produce V$_{5+}$ ions. The benzyl alcohol in turn acted as a reductant under refluxing to reduce the mixture of V$^{4+}$ cations and V$^{5+}$ cations to V$^{4+}$ cations. The various dopant of promoter compounds, containing the various dopant or promoter metals, were added, after the V$_2$O$_5$ was added, to the solvent from which the catalyst precursor was eventually precipitated upon cooling to room temperature after the stirring and refluxing were completed.

In the case of Examples 2–13 the oven-dried blue precursor was in each case calcined according to the procedure and heating regime described in Example 1 to obtain various novel VPO catalysts. These novel catalysts were tested regarding their ability to catalyze conversion of butane to maleic anhydride, butene to maleic anhydride, phthalic anhydride and acetic acid, and pentene to maleic anhydride, phthalic anhydride and acetic acid, and in each case the novel catalysts were found to out-perform the standard or control catalyst with which they were compared, with regard to one or more of percentage butane conversion, percentage selectively to produce maleic anhydride or percentage yield.

It has also been found that by varying either the temperature or gas hourly space velocity or both, the selectivity to maleic anhydride and phthalic anhydride can be varied, as set forth in Table 3 hereunder.

TABLE 3

Comparison of Novel VPO Catalysts at Equilibration

| | Butane | Butene | Pentane | Pentene |
|---|---|---|---|---|
| Gas hourly space velocity (h$^{-1}$) | 1500–3000, preferably 2000–2600 | 1500–3000, preferably 2000–2600 | 750–2000, preferably 800–1500 | 750–2000, preferably 800–1500 |
| Temperature (° C.) | 350–450 preferably 380–410 | 350–450 preferably 380–410 | 320–380 preferably 330–350 | 350–450 preferably 380–410 |
| % Conversion | 70–80 | 75–90 | 70–88 | 70–95 |
| % Maleic anhydride selectivity | 60–76 | 60–70 | 30–50 | 30–60 |
| % Phthalic anhydride selectivity | — | — | 5–15 | 10–20 |

What is claimed is:

1. A method of making a vanadium phosphorus oxide (VPO) catalyst, the method comprising the steps of:
   precipitating, from a solution comprising dissolved V$^{4+}$ ions and V$^{5+}$ ions at a total concentration of 45–65 g/l, a vanadium-containing and phosphorus-containing precipitate comprising a complex in accordance with the formula VOHPO$_4$.½H$_2$O; and calcining the precipitate under an inert atmosphere, to produce a VPO catalyst having an active phase in accordance with the formula $(VO)_2P_2O_9$, the solution from which the precipitate is precipitated comprising dissolved cations of at least two dopant metals selected from the group of metals consisting of Bi, Zr, Cr, Ce, Co, Mn, Mg and Mo, said dissolved dopant metal cations being present in the solution in proportions such that the precipitate comprises 1–25% by mass of dopant metal cations in total, the balance being the $VOHPO_4.½H_2O$ complex, each dopant metal forming 0.1–20% by mass of the precipitate, the dopant metal cations being present in the solution as a mixture of cations of different dopant metals, wherein, if said mixture of cations consist of cations of three different dopant metals, the three different dopant metals are selected from the group consisting of:

Bi and Zr and Cr;
Bi and Zr and Ce;
Bi and Zr and Co;
Bi and Zr and Mn;
Bi and Zr and Mg;
Bi and Zr and Mo;
Bi and Cr and Ce;
Bi and Cr and Co;
Bi and Cr and Mn;
Bi and Cr and Mg;
Bi and Cr and Mo;
Bi and Ce and Co;
Bi and Ce and Mn;
Bi and Ce and Mg;
Bi and Ce and Mo;
Bi and Co and Mn;
Bi and Co and Mg;
Bi and Co and Mo;
Bi and Mn and Mg;
Bi and Mn and Mo;
Bi and Mg and Mo;
Zr and Cr and Ce;
Zr and Cr and Mn;
Zr and Cr and Mg;
Zr and Cr and Mo;
Zr and Ce and Co;
Zr and Ce and Mn;
Zr and Ce and Mg;
Zr and Ce and Mo;
Zr and Co and Mn;
Zr and Co and Mg;
Zr and Co and Mo;
Zr and Mn and Mg;
Zr and Mn and Mo;
Zr and Mg and Mo;
Cr and Ce and Co;
Cr and Ce and Mn;
Cr and Ce and Mg;
Cr and Ce and Mo;
Cr and Co and Mn;
Cr and Co and Mg;
Cr and Co and Mo;
Cr and Mn and Mg;
Cr and Mn and Mo;
Cr and Mg and Mo;
Ce and Co and Mn;
Ce and Co and Mg;
Ce and Co and Mo;
Ce and Mn and Mg;
Ce and Mn and Mo;
Ce and Mg and Mo;
Co and Mn and Mo;
Co and Mg and Mo; and
Mn and Mg and Mo, and wherein, if said mixture of cations consists of cations of two different dopant metals, the two different dopant metals are selected from the group consisting of:

Bi and Zr;
Bi and Cr;
Bi and Ce;
Bi and Co;
Bi and Mn;
Bi and Mg;
Bi and Mo;
Zr and Ce;
Zr and Mn;
Zr and Mg;
Zr and Mo;
Cr and Ce;
Cr and Mn;
Cr and Mg;
Cr and Mo;
Ce and Co;
Ce and Mn;
Ce and Mg;
Ce and Mo;
Co and Mo;
Mn and Mo; and
Mg and Mo.

2. A method as claimed in claim 1, in which the total concentration of dissolved $V^{4+}$ and $V^{5+}$ ions in the solution is 50–60 g/l, the dissolved dopant metal cations being present in the solution in proportions such that the precipitate comprises 2–20% by mass of the dopant metals in total, each dopant metal forming 0.5–15% by mass of the precipitate, the ratio of dissolved $V^{4+}$ ions:$V^{5+}$ ions in the solution being such that the molar proportion of the $V^{5+}$ ions in the total vanadium ion content of the VPO catalyst is 0.1–10 mole %.

3. A method as claimed in claim 2, in which the solution from which the which the precipitate is precipitated comprises dissolved cations of two to three dopant metals selected from said group consisting of Bi, Zr, Cr, Ce, Co, Mn, Mg and Mo.

4. A method as claimed in claim 3, in which one of the dopant metals is Bi, Bi cations being present in the solution from which the precipitate is precipitated in a proportion such that Bi forms 1–15% by mass of the precipitate, the solution comprising, in addition to the Bi cations, cations of one to two other dopant metals selected from:

Zr;
Mn and Ce;
Cr;

Ce;
Zr and Ce; and
Zr and Co.

5. A method as claimed in claim 3, in which one of the dopant metals is Zr, Zr cations being present in the solution from which the precipitate is precipitated in a proportion such the Zr forms 1–15% by mass of the precipitate, the solution comprising, in addition to the Zr cations, cations of one to two other dopant metals, selected from:
Bi;
Ce and Cr;
Ce;
Bi and Ce; and
Bi and Co.

6. A method as claimed in claim 3, in which one of the dopant metals is Cr, Cr cations being present in the solution from which the precipitate is precipitated in a proportion such that Cr forms 1–15% by mass of the precipitate, the solution comprising, in addition to the Cr cations, cations of Ce and Zr.

7. A method as claimed in claim 3, in which one of the dopant metals is Ce, Ce cations being present in the solution from which the precipitate is precipitated in a proportion such that Ce forms 1–15% by mass of the precipitate, the solution comprising, in addition to the Ce cations, cations of one to two other dopant metals, selected from:
Zr and Cr;
Zr;
Bi and Mn;
Bi;
Bi and Zr; and
Mn and Mg.

8. A method as claimed in claim 3, in which one of the dopant metals is Co, Co cations being present in the solution from which the precipitate is precipitated in a proportion such that Co forms 1–15% by mass of the precipitate, the solution comprising, in addition to the Co cations, cations of one to two other dopant metals, selected from:
Bi; and
Bi and Zr.

9. A method as claimed in claim 3, in which one of the dopant metals in Mn, Mn cations being present in the solution from which the precipitate is precipitated in a proportion such that Mn forms 1–15% by mass of the precipitate, the solution comprising, in addition to the Mn cations, cations of one to two other dopant metals, selected from:
Bi and Ce;
Mg and Ce; and
Mo.

10. A method as claimed in claim 3, in which one of the dopant metals is Mg, Mg cations being present in the solution from which the precipitate is precipitated in a proportion such that Mg forms 1–20% by mass of the precipitate, the solution comprising cations of Mn and Ce dopant metals in addition to the Mg cations.

11. A method as claimed in claim 3, in which one of the dopant metals is Mo, Mo cations being present in the solution from which the precipitate is precipitated in a proportion such that Mo forms 1–20% by mass of precipitate, the solution comprising cations of Mn dopant metal in addition to the Mo cations.

12. A method as claimed in claim 1, in which the solution comprises a solvent selected from alcohols and mixtures of two or more alcohols.

13. A method as claimed in claim 12, in which the solvent is a mixture of two alcohols, the alcohols being present in a mass ratio of 1:2–2:1.

14. A method as claimed in claim 12, in which the solvent is anhydrous, each alcohol being selected from:
isobutanol;
benzyl alcohol;
ethanol;
octanol;
2-butanol;
isopropanol; and
mixtures of any two or more thereof.

15. A method as claimed in claim 14, in which the solvent is a mixture of two said alcohols.

16. A method as claimed in claim 1, which includes the preliminary step of obtaining the solution of the $V^{4+}$ ions and $V^{5+}$ ions in the solution by dissolving $V^{5+}$ ions in the solvent and reducing a portion of the $V^{5+}$ ions to $V^{4+}$ ions.

17. A method as claimed in claim 16, in which the reducing of the $V^{5+}$ ions to $V^{4+}$ ions is by means of a reducing agent, the method including refluxing the solvent containing the $V^{5+}$ ions dissolved therein with the reducing agent.

* * * * *